US012697084B2

(12) United States Patent
Jiang et al.

(10) Patent No.: US 12,697,084 B2
(45) Date of Patent: Aug. 4, 2026

(54) DETERMINING COUCH FRAME SHIFT

(71) Applicant: KONINKLIJKE PHILIPS N.V.,
Eindhoven (NL)

(72) Inventors: Xin X Jiang, Liaoning Province (CN);
Cheng Bo Yao, Liaoning Province
(CN); Qi Fu Cheng, Yuanyangziran
(CN)

(73) Assignee: KONINKLIJKE PHILIPS N.V.,
Eindhoven (NL)

( * ) Notice: Subject to any disclaimer, the term of this
patent is extended or adjusted under 35
U.S.C. 154(b) by 189 days.

(21) Appl. No.: 18/291,687

(22) PCT Filed: Jul. 8, 2022

(86) PCT No.: PCT/EP2022/069110
§ 371 (c)(1),
(2) Date: Jan. 24, 2024

(87) PCT Pub. No.: WO2023/006385
PCT Pub. Date: Feb. 2, 2023

(65) Prior Publication Data
US 2024/0237962 A1      Jul. 18, 2024

(30) Foreign Application Priority Data

Jul. 26, 2021      (WO) ................ PCT/CN2021/108447
Oct. 15, 2021      (EP) ..................................... 21202884

(51) Int. Cl.
A61B 6/00          (2024.01)
A61B 6/04          (2006.01)
A61G 13/02          (2006.01)

(52) U.S. Cl.
CPC .......... A61B 6/5276 (2013.01); A61B 6/0407
(2013.01); A61G 13/02 (2013.01);
(Continued)

(58) Field of Classification Search
CPC .. A61G 2210/50; A61G 13/02; A61N 5/1069;
A61B 6/0407; A61B 6/0487; A61B
6/5276
See application file for complete search history.

(56) References Cited

U.S. PATENT DOCUMENTS

2008/0289106 A1*  11/2008  Beyer ................. A61B 6/5276
5/601
2009/0003522 A1*  1/2009  Chien ................. A61N 5/1049
378/65

(Continued)

FOREIGN PATENT DOCUMENTS

DE      102007060690 A1      6/2009
JP      S6373936 A      4/1988
(Continued)

OTHER PUBLICATIONS

PCT International Search Report, International application No.
PCT/EP2022/069110, Nov. 8, 2022.

*Primary Examiner* — David J Makiya
*Assistant Examiner* — Soorena Kefayati
(74) *Attorney, Agent, or Firm* — Larry Liberchuk

(57) ABSTRACT

To improve accuracy of positioning a patient relative to an
imagining apparatus, an indication of a weight on a move-
able support of a couch assembly is received, where the
moveable support is moveable relative to a couch frame of
the couch assembly. Then, an indication of an expected
position for the moveable support to move to a modified
position relative to the couch frame is received to provide
the moveable support at a specified position relative to the
imaging apparatus. After that, a horizontal shift of the couch
frame is determined for the expected position relative to an
imaging apparatus associated with the couch assembly based
on a shift model indicative of the horizontal shift as a
function of the weight on the moveable support and a
(Continued)

horizontal position of the moveable support relative to the couch frame.

14 Claims, 6 Drawing Sheets

(52) U.S. Cl.
CPC ...... *A61G 2203/10* (2013.01); *A61G 2203/44* (2013.01); *A61G 2210/50* (2013.01)

(56) References Cited

U.S. PATENT DOCUMENTS

| | | | | |
|---|---|---|---|---|
| 2009/0144902 | A1* | 6/2009 | Baumann | A61B 6/0487 700/60 |
| 2010/0287703 | A1* | 11/2010 | Zapata | A61B 6/5276 5/607 |
| 2012/0023671 | A1* | 2/2012 | Miyano | A61B 6/0407 5/601 |
| 2014/0336500 | A1* | 11/2014 | Katsunuma | A61B 5/055 600/415 |
| 2014/0364718 | A1* | 12/2014 | Teshigawara | A61B 6/0407 600/407 |
| 2015/0135437 | A1* | 5/2015 | Li | A61B 6/5276 5/601 |
| 2016/0000388 | A1* | 1/2016 | Metzler | A61B 6/4258 250/363.02 |
| 2016/0015353 | A1* | 1/2016 | Kim | A61B 6/542 378/68 |
| 2016/0113598 | A1* | 4/2016 | Dong | A61B 6/0487 600/407 |
| 2016/0143607 | A1* | 5/2016 | Cao | A61B 6/5276 378/20 |
| 2016/0151025 | A1* | 6/2016 | Gatayama | G01T 1/1603 378/209 |
| 2017/0020466 | A1* | 1/2017 | Moulin | A61B 6/0442 |
| 2017/0095219 | A1* | 4/2017 | Wakahara | A61B 6/0487 |
| 2017/0119277 | A1* | 5/2017 | Wu | A61B 5/70 |
| 2017/0312159 | A1* | 11/2017 | Fliege | F16C 29/10 |
| 2018/0078223 | A1* | 3/2018 | Oishi | A61B 6/0487 |
| 2018/0289575 | A1* | 10/2018 | Hiratsuka | A61G 13/104 |
| 2018/0339172 | A1* | 11/2018 | Stahl | A61N 5/1069 |
| 2019/0175942 | A1* | 6/2019 | Stahl | A61B 6/032 |
| 2020/0170869 | A1* | 6/2020 | Kohler | A61G 13/06 |
| 2020/0306563 | A1* | 10/2020 | Hara | A61N 5/1079 |
| 2021/0228175 | A1* | 7/2021 | Siegel | A61B 6/037 |
| 2022/0047218 | A1* | 2/2022 | Neuber | A61B 5/704 |

FOREIGN PATENT DOCUMENTS

| | | |
|---|---|---|
| JP | H07284494 A | 10/1995 |
| JP | 2007159719 A | 6/2007 |
| JP | 2013027476 A | 2/2013 |
| WO | WO2019056134 A1 | 3/2019 |

* cited by examiner

200

300

400

500

DETERMINING COUCH FRAME SHIFT

TECHNICAL FIELD OF THE INVENTION

The invention relates to a method, a tangible machine-readable medium and apparatus for determining shift of a couch frame associated with an imaging apparatus.

BACKGROUND OF THE INVENTION

During a patient imaging operation, a moveable support of a couch assembly may move a patient to a specified position so that an imaging apparatus such as a computed tomography (CT) scanner may obtain imaging data at an imaging plane corresponding to a specified part of the patient's body. However, the accuracy of positioning of the patient with respect to the imaging plane may affect the outcome of the imaging operation. For example, if there is an error in the position of the patient relative to the imaging plane, the imaging data may not correspond to the specified part of the patient. In some cases, the patient may need to be moved again so that the specified part of the patient is imaged, which may unnecessarily increase patient exposure to radiation and/or increase the time spent performing the imaging operation. In some cases, the error may not be recognized, which may lead to an incorrect analysis of the imaging data. The error of patient position relative to imaging plane in a vertical direction has been discussed in DE102007060690A1 and US 20160113598.

SUMMARY OF THE INVENTION

Aspects or embodiments described herein may relate to improving the accuracy of positioning a subject such as a patient relative to an imaging apparatus. Aspects or embodiments described herein may obviate one or more problems associated with or arising from inaccurate positioning of a subject during an imaging operation.

In a first aspect, a method is described. The method is a computer-implemented method. The method comprises receiving an indication of a weight on a moveable support of a couch assembly. The moveable support is moveable relative to a couch frame of the couch assembly. The method further comprises determining a horizontal shift of the couch frame relative to an imaging apparatus associated with the couch assembly based on a shift model indicative of the horizontal shift as a function of: the indicated weight on the moveable support; and a horizontal position of the moveable support relative to the couch frame.

Some embodiments relating to the first and other aspects are described below.

In some embodiments, the method comprises receiving an indication of an expected position for the moveable support to move to relative to the couch frame to provide the moveable support at a specified position relative to the imaging apparatus. The method further comprises determining the horizontal shift for the expected position.

In some embodiments, the method comprises causing the moveable support to move to a modified position determined based on a difference between the expected position and the horizontal shift, such that the moveable support is provided at the specified position.

In some embodiments, causing the moveable support to move to the modified position comprises causing a moveable support actuator of the couch assembly to move the moveable support to the modified position.

In some embodiments, causing the moveable support to move to the modified position comprises: generating a command configured to cause the moveable support actuator to move the moveable support to the modified position; and sending the command to the moveable support actuator to cause actuation of the moveable support actuator according to the command.

In some embodiments, the moveable support actuator is configured to move the moveable support in a horizontal direction relative to a surface supporting the couch assembly, such that the moveable support is provided at the specified position.

In some embodiments, the indication of the weight comprises an indication of electrical current supplied to a couch frame actuator of the couch assembly. The couch frame actuator may be configured to control a height of the moveable support relative to a surface supporting the couch assembly.

In some embodiments, the couch frame actuator is configured to maintain the moveable support at a specified height during horizontal movement of the moveable support relative to the couch frame.

In some embodiments, the method comprises receiving the indication of the weight by receiving the indication of the electrical current. The method may further comprise estimating the weight by using a vertical force balancing model of the electrical current needed to provide the moveable support at a specified height. The method may further comprise receiving a command specifying an expected position to which the moveable support is to move to relative to the couch frame. The method may further comprise determining an expected shift of the couch frame according to the shift model based on the estimated weight and the expected position. The method may further comprise generating a revised, or 'modified', command specifying a modified position to which the moveable support is to move to relative to the couch frame based on a difference between the expected position and the expected shift for the expected position.

In some embodiments, the shift model is determined from a set of measured values for the horizontal shift and a corresponding set of indicated values for the horizontal position of the moveable support where the horizontal shift is measured.

In some embodiments, the shift model is based on a linear function fitted to the set of measured values for the horizontal shift and the corresponding set of indicated values for the horizontal position of the moveable support.

In some embodiments, the shift model is determined from the set of indicated values for the horizontal position of the moveable support at each of a set of indicated values for the weight on the moveable support.

In a second aspect, a tangible machine-readable medium is described. The tangible machine-readable medium comprises instructions which, when executed by at least one processor, cause the at least one processor to perform the method of the first aspect or any related embodiment.

In a third aspect, apparatus is described. The apparatus comprises at least one processor communicatively coupled to an interface configured to receive an indication of a weight on a moveable support of a couch assembly. The moveable support is moveable relative to a couch frame of the couch assembly. The apparatus further comprises a tangible machine-readable medium storing instructions readable and executable by the at least one processor to perform a method. The method comprises receiving the indication of the weight. The method further comprises determining a horizontal shift of the couch frame relative to an imaging apparatus associated with the couch assembly based on a shift model indicative of the horizontal shift as a function of: the indicated weight on the moveable support; and a horizontal position of the moveable support relative to the couch frame.

An embodiment relating to the third aspect and other aspects is described below.

In some embodiments, the interface is further configured to receive an indication of an expected position for the moveable support to move to relative to the couch frame to provide the moveable support at a specified position relative to the imaging apparatus. The interface may further be configured to send a command to a moveable support actuator of the couch assembly. The command may be configured to actuate the moveable support actuator. The instructions may further comprise instructions readable and executable by the at least one processor to perform a method. The method comprises receiving the indication of the expected position. The method may further comprise determining the horizontal shift for the expected position. The method may further comprise causing the moveable support to move to a modified position determined based on a difference between the expected position and the horizontal shift, such that the moveable support is provided at the specified position, by: generating the command configured to cause the moveable support actuator to move the moveable support to the modified position; and sending the command, via the interface, to the moveable support actuator to cause actuation of the moveable support actuator according to the command.

These and other aspects of the invention will be apparent from and elucidated with reference to the embodiment(s) described hereinafter.

BRIEF DESCRIPTION OF DRAWINGS

Exemplary embodiments of the invention will now be described, by way of example only, with reference to the following drawings, in which.

DETAILED DESCRIPTION OF THE EMBODIMENTS

Figure 1:
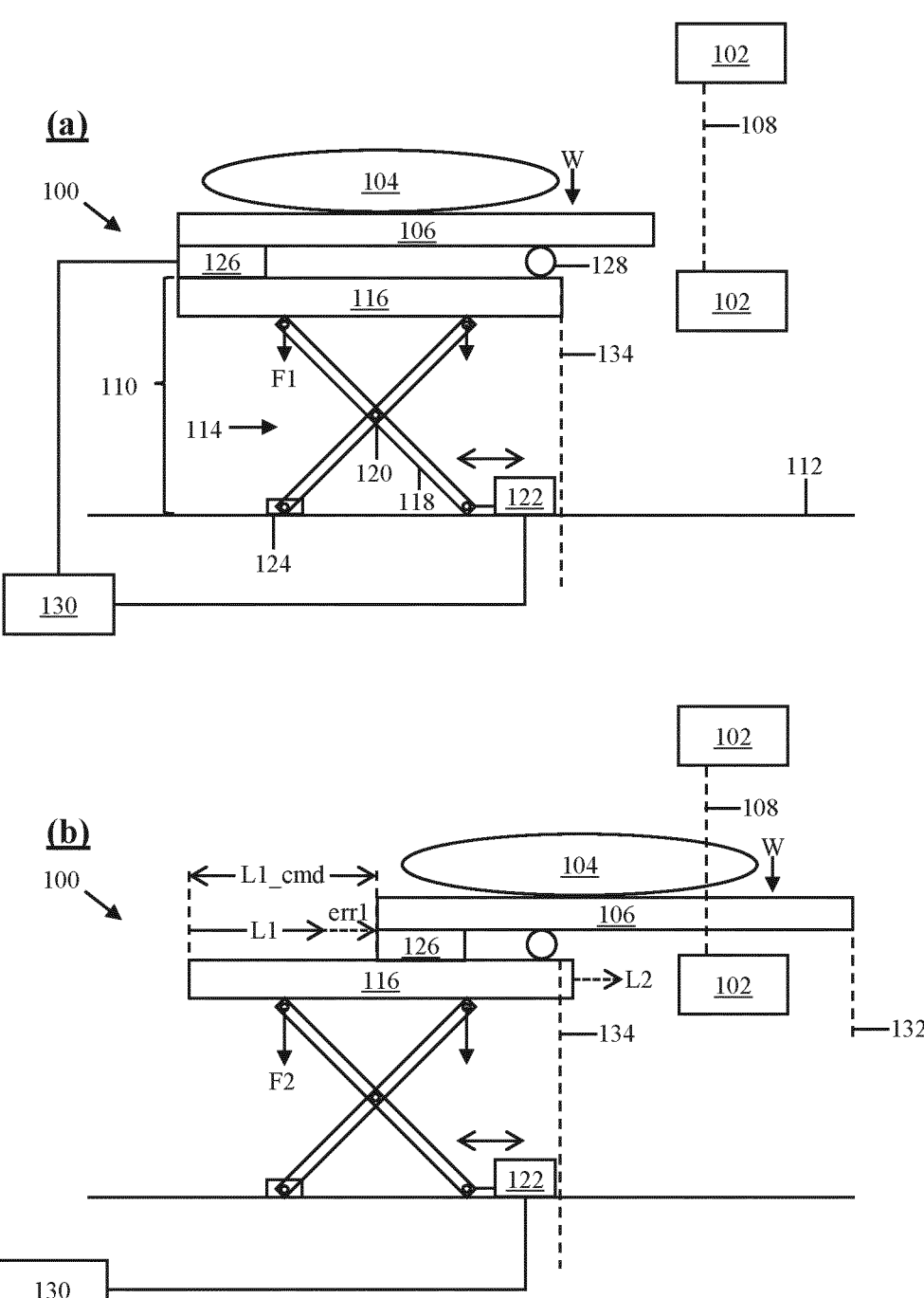
FIG. 1 is a schematic drawing of a scenario depicting an error in positioning of a moveable support of a couch assembly, as referred to in various embodiments.

FIG. 1 is a schematic drawing of an example couch assembly 100 associated with an imaging apparatus 102 such as a computed tomography (CT) scanner. The couch assembly 100 is used to support a subject 104 such as a patient. Two configurations, (a) and (b), of the couch assembly 100 are shown. For ease of illustration, certain reference signs or connecting elements are not shown in both configurations.

As shown by configuration (a), the subject 104 is positioned on a moveable support 106 of the couch assembly 100. The moveable support 106 may sometimes be referred to as a 'table', 'table top' or 'couch'. As shown by configuration (b), movement of the moveable support 106 from the position shown in configuration (a) has positioned the subject 104 in an imaging plane 108 associated with the imaging apparatus 102. Thus, by moving the moveable support 106 relative to the imaging plane 108, different parts of the subject 104 may be imaged. For example, multiple imaging 'slices' may be obtained at different axial positions along the subject 104 by moving the subject 104 relative to the imaging plane 108 and acquiring an image at each of the axial positions.

The couch assembly 100 also comprises a couch frame 110 for supporting the moveable support 106 and facilitating movement (e.g., horizontal movement) of the moveable support 106 relative to the imaging apparatus 102. The couch frame 110 is configured to balance the weight, W, of the subject 104 (and any other equipment supported by the moveable support 106) so that the subject 104 can be positioned at a specified distance (e.g., height) above a surface 112 such as the floor upon which the couch assembly 100 is positioned.

In this example couch assembly 100, the couch frame 110 comprises a scissor mechanism 114 for supporting a base member 116 upon which the moveable support 106 is mounted. Other mechanisms are possible as described below. In this example, the scissor mechanism 114 comprises two ('lever') members 118 which are configured to lever relative to each other via a pivot 120 at the center of each member 118.

One end of each member 118 is pivotally connected to the base member 116 while another end of each member 118 is pivotally mounted on the surface 112. The ends of the two members 118 pivotally connected to the base member 116 are moveably spaced apart from each other so that the base member 116 is appropriately supported by the scissor mechanism 114 (e.g., so that the base member 116 is parallel to the surface 112). Similarly, the other ends of the two members 118 pivotally mounted on the surface 112 are moveably spaced apart from each other. The couch assembly 100 comprises a couch frame actuator 122 (e.g., an electric motor) configured to control/adjust the height of the subject 104 by causing the members 118 to lever relative to each other (while also causing relative movement between the ends of the members 118 connected to the base member 116). In this embodiment, the couch frame actuator 122 is mounted on the surface 112 and is configured to apply a force to the end of one of the members 118 mounted on the surface 112. The end of the other member 118 mounted on the surface 112 is fixed in place, as indicated by fixed mount 124.

Thus, in use, the couch frame actuator 122 may apply a force on the member 118 to cause the ends of the members 118 mounted on the surface 112 to move closer together. Due to the lever motion about the pivot 120, this movement of the members 118 raises the base member 116, hence also raising the subject 104. The weight, W, may be balanced using a specified force applied by the couch frame actuator 122. By varying this force, the subject 104 may be raised or lowered relative to the surface 112. In the case that the couch frame actuator 122 comprises an electric motor, the electrical current supplied to the electric motor may be varied to controllably adjust the height of the subject 104.

As highlighted above, the configuration of the scissor mechanism 114 and associated parts of the couch assembly 100 may differ to that shown and described in relation to FIG. 1. For example, the two members 118 may not be configured in a scissor-like arrangement as shown by FIG. 1 but instead may move independently of each other (e.g., the members 118 may not be connected to each other via a pivot 120). Further, the number of members 118 may differ (e.g., more than two members 118 may be used or one member may be used). Further, the configuration of the couch frame actuator 122 may be different (e.g., the couch frame actuator 122 may be connected to a different part of the member 118, etc.).

Therefore, in terms of function, the couch assembly 100 is configured to facilitate adjustment/control of the height of the subject 104 while balancing the weight, W, so that the subject 104 can be provided at the specified height. Any configuration of couch assembly 100 that facilitates such a function may be relevant to this disclosure.

It shall be appreciated that the configuration shown in FIG. 1 is schematic to better illustrate possible components of the couch assembly 100 and therefore the configuration and design of the components may differ to that shown by FIG. 1.

As will now be described, the configuration of the couch assembly 100 may lead to an error in terms of the positioning of the subject 104 relative to the imaging apparatus 102.

The couch assembly 100 comprises a moveable support actuator 126 for moving the moveable support 106 relative to the couch frame 110. In this example, the moveable support actuator 126 is mounted between the base member 116 and the moveable support 106. In use, the moveable support actuator 126 (such as an electric motor, hydraulic system, etc.) applies a force between the base member 116 and the moveable support 106 to cause relative movement therebetween. The moveable support 106 is mounted on a sliding mechanism 128 (e.g., at least one roller) mounted on the base member 116 to facilitate movement (e.g., sliding movement) between the moveable support 106 and the base member 116.

In order to move between the configurations, (a) and (b), a command ('L1_cmd') is sent by a controller 130 communicatively coupled to the moveable support actuator 126 to cause the moveable support 106 to move a distance 'L1' so that the end of the moveable support 106 overhanding the couch frame 110 is at a specified position 132 (which means that the subject 104 is provided at a specified position defined by the command, L1_cmd). There may be an error, 'err1', in the actual distance moved. Therefore, a correcting mechanism such as a servo motor (not shown) may correct for this error, err1.

The controller 130 (or a different controller) may also be communicatively coupled to the couch frame actuator 122. Therefore, in use, the controller 130 may send commands to the couch frame actuator 122 to control/adjust the vertical position (e.g., height) of the subject 104 and/or the moveable support actuator 126 to control/adjust the position (e.g., horizontal position) of the subject 104 relative to the imaging apparatus 102. The controller 130 may receive feedback from the couch frame actuator 122 and/or moveable support actuator 126 such as an indication of electrical current supplied and/or an indication of the configuration of the couch frame actuator 122 and/or moveable support actuator 126.

Between the two configurations, (a) and (b), a position of the center of gravity is shifted when the subject 104 is moved, by the moveable support 106, towards and into the imaging plane 108 so that the end of the moveable support 106 overhanging the couch frame 110 is provided at the specified position 132.

In configuration (a), a force F1 acts on the couch frame 110 at the point indicated in FIG. 1 (i.e., where the ends of the members 118 are connected to the base member 116).

In configuration (b), a larger force F2 acts on the couch frame 110 at the same point since the center of gravity has shifted to a position that is no longer acting over the center of the couch frame 110, as depicted by configuration (a).

This larger force F2 leads to additional compression of the couch frame 110 with a corresponding horizontal shift of the couch frame 110. This leads to movement of the couch frame 110, relative to the surface 112, towards the imaging apparatus 102. In some cases, this compression may also result in a (relatively small) reduction in the height of the couch frame 110. As shown by configuration (b), the position of the couch frame 110 is shifted by a distance, L2, from the previous position of the couch frame 110. In particular, the end the base member 116 in configuration (a) is indicated by line 134 in configuration (b). The distance between the end of the base member 116 and the line 134 corresponds to the shift, L2. Thus, the larger the distance, L1, the larger the distance, L2, since more force acts on the couch frame 110 due to shifted center of gravity causing an increase in the lever effect acting on the scissor mechanism 114.

However, it may not be possible for the correcting mechanism for correcting the error, err1, associated with L1 to correct for the shift, L2.

While in configuration (a), the motion control reference frame of the moveable support 106 is based on the couch frame 110 (i.e., the movement of the moveable support 106 is defined with respect to a frame of reference defined by the couch frame 110). However, the reference frame of the couch frame 110 itself is defined in relation to the surface 112 (e.g., a 'ground' reference frame). Similarly, the imaging apparatus 102 is fixed in relation to the surface 112. Thus, if it is assumed that the couch frame 110 and imaging apparatus 102 are fixed relative to each other, then movement of the moveable support 106 is relative to the surface 112 itself. For example, when the couch frame 110 is not shifted, as indicated by configuration (a), the frame of reference of the moveable support 106 and couch frame 110 is the same.

However, when the couch frame 110 is shifted as indicated by configuration (b), a deviation/offset is introduced which means that the assumption about the frames of reference cannot be relied upon to ensure accurate positioning of the subject 104 relative to the imaging apparatus 102. The deviation/offset may affect the quality and/or outcome of the imaging operation. In some cases, the deviation may be such that additional images need to be acquired, which may unnecessarily increase patient exposure to radiation and/or increase the time spent performing the imaging operation. In some cases, the error may not be recognized, which may lead to an incorrect analysis of the imaging data.

At present, the deviation/offset of the couch frame 110 is not considered and therefore a systematic error may be introduced that is proportional to the movement distance, L1. Embodiments described herein may facilitate correction of this deviation/offset. For example, certain embodiments described herein may determine the couch frame shift.

Certain embodiments may take action to correct for the determined couch frame shift.

Figure 2:
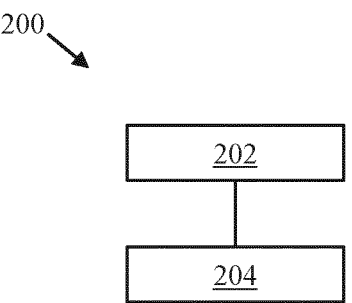
FIG. 2 refers to a method of determining couch frame shift according to an embodiment.

FIG. 2 shows a method 200 (e.g., a computer-implemented method) of determining couch frame shift according to an embodiment. In the discussion of method 200, reference is made to FIG. 1. FIG. 1 depicts a controller 130 which may implement the method 200. The controller 130 may be implemented by a computer such as a user computer communicatively coupled to a user interface, or a server or cloud-based service (e.g., communicatively coupled to the user computer and/or user interface). Thus, the method 200 may be implemented in situ (e.g., on a user computer in the locality of the couch assembly 100) or in another location (e.g., on a server or in the cloud). Commands and/or feedback may be communicated between the controller 130 and the couch frame actuator 122 and/or moveable support actuator 126 to facilitate the implementation of certain methods described herein (e.g., method 200).

The method 200 comprises, at block 202, receiving an indication of a weight on a moveable support 106 of a couch assembly 100. The moveable support 106 is moveable relative to a couch frame 110 of the couch assembly 100. Further discussion on the indication of the weight is provided below.

The method 200 further comprises, at block 204, determining a shift, L2, of the couch frame 110 relative to an imaging apparatus 102 associated with the couch assembly 100. The determination of the shift, L2, is based on a shift model (a description of which is given below) indicative of the shift as a function of: the indicated weight on the moveable support 106; and a position of the moveable support 106 relative to the couch frame 110. The position of the moveable support 106 may be defined in relation to the distance L1 moved. For example, the end of the moveable support 106 is at the specified position 132 according to the distance L1 moved.

The method 200 may allow the couch frame shift to be determined.

Accordingly, as will be described in more detail below, a correction can be applied to the command, L1_cmd, to ensure that the subject 104 is provided at a specified position. For example, during an imaging operation, an operator may command the moveable support 106 to move to a specified position (e.g., defined by a fixed point such as the end of the moveable support 106 being provided at the specified position 132). However, to correct for the couch frame shift which may otherwise lead to the subject 104 being moved to an incorrect (e.g., unexpected) position, the command may be modified to take into account the (expected) couch frame shift so that the subject 104 is moved to a correct (e.g., expected or specified) position.

Such a correction may improve the quality and/or outcome of the imaging operation. In some cases, the correction may avoid the need to acquire additional images. In some cases, the correction may improve the quality and/or outcome of analysis of the imaging data.

Figure 3:
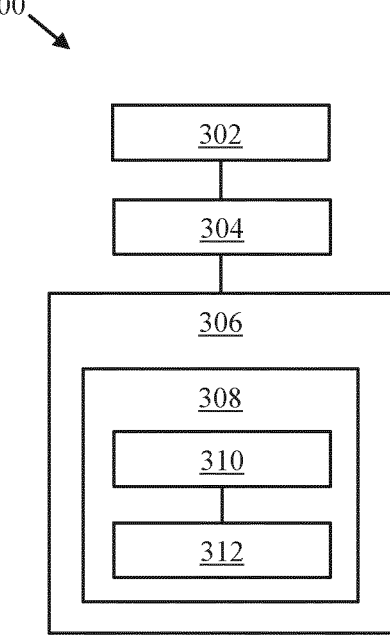
FIG. 3 refers to a method of determining and correcting for couch frame shift according to various embodiments.

FIG. 3 shows a method 300 (e.g., a computer-implemented method) of determining and correcting for couch frame shift according to various embodiments. The method 300 may be implemented in the same way as method 200 (e.g., using the controller 130). For example, the method 300 may comprise the same or similar functionality as the method 200. Reference is made to FIGS. 1 and 2, where appropriate. Certain blocks of the method 300 may not need to be implemented and/or certain blocks of the method 300 may be performed in a different order to that shown by FIG. 3.

In some embodiments, the method 300 comprises, at block 302, receiving 302 an indication of an expected position for the moveable support 106 to move to relative to the couch frame 110 to provide the moveable support 106 at a specified position 132 relative to the imaging apparatus 102. The 'expected position' may refer to a position to which the moveable support 106 is to move (i.e., after the command, L1_cmd, has been executed). The 'expected position' is based on the assumption that the frame of reference of the couch frame 110 does not shift upon moving the moveable support 106 to the specified position 132. However, the command, L1_cmd, may not lead to the moveable support 106 being moved to the specified position 132. Rather, the command L1_cmd does not take into account the shift described above. Thus, the method 300 further comprises, at block 304, determining the shift for the expected position (e.g., in accordance with the method 200).

In some embodiments, the method 300 comprises, at block 306, causing the moveable support 106 to move to a modified position determined based on a difference between the expected position and the shift, such that the moveable support 106 is provided at the specified position 132 (i.e., as expected). Thus, the 'modified position' takes into account the shift, L2. In other words, if the couch frame is shifted by L2 then the command, L1_cmd, may be modified to take this into account. For example, if the shift is a distance L2, then the command may specify that the moveable support 106 is to move by a distance L1-L2. As a result of this modified command, the subject 104 may be positioned correctly, or as expected (since the modified position, L1-L2, of the moveable support 106 relative to the couch frame 110 results in the moveable support 106 being correctly provided at the specified position 132).

In some embodiments, causing the moveable support 106 to move to the modified position comprises, at block 308, causing the moveable support actuator 126 of the couch assembly 100 to move the moveable support 106 to the modified position.

In some embodiments, the method 300 of causing the moveable support to move to the modified position according to block 308 comprises, at block 310, generating a command configured to cause the moveable support actuator 126 to move the moveable support 106 to the modified position (e.g., with respect to the frame of reference defined by the couch frame 110). Block 308 further comprises, at block 312, sending the command to the moveable support actuator 126 to cause actuation of the moveable support actuator 126 according to the command.

In some embodiments, the moveable support actuator 126 is configured to move the moveable support 106 in a horizontal direction relative to the surface 112 supporting the couch assembly 100, such that the moveable support 106 (e.g., the end of the moveable support 106 overhanging the couch frame 110) is provided at the specified position 132.

In some embodiments, the couch frame actuator 122 is configured to control a height of the moveable support 106 relative to the surface 112.

In some embodiments, the indication of the weight comprises an indication of electrical current supplied to the couch frame actuator 122.

In some embodiments, the couch frame actuator 122 is configured to maintain the moveable support 106 at a specified height during horizontal movement of the moveable support 106 relative to the couch frame 110.

An embodiment describing estimation of the weight (used to provide the indication of the weight) is described in more detail below.

Figure 4:
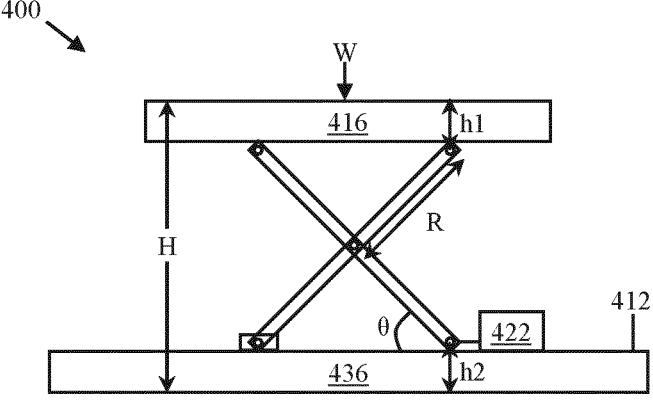
FIG. 4 is a schematic drawing depicting a model of a couch assembly for estimating weight.

FIG. 4 shows a simplified illustration of a couch assembly 400 similar to the couch assembly 100 depicted by FIG. 1. Reference signs for features of the couch assembly 400 that are the same as or similar to corresponding features of the couch assembly 100 are incremented by 300. Some features are not shown or described for ease of illustration and reference is made to FIG. 1, where appropriate.

The couch assembly 400 has a scissor mechanism, which can be modeled to determine the weight, W. The weight, W, of the components of the couch assembly 400 such as the base member 416 and moveable support (not shown) are fixed. However, the weight may vary depending on the weight of the subject and any other equipment (not shown) provided on the moveable support 106.

The couch frame actuator 422 is used to balance the vertical force applied due to the weight of the components and the subject, etc. In case the couch frame actuator 422 comprises an electric motor for applying a force to balance the vertical force, the electrical current supplied to the electric motor may be varied accordingly. Based on the electrical current feedback, the weight, W, can be estimated using the following vertical force balancing model:

$$\theta = \arcsin\left((H - h1 - h2)/2R\right)$$

$$F = W * g * 2 * \frac{R}{r} * \cos\theta * (1 - \cos\theta)$$

$$F * p = T * i * 2 * \pi * \eta_T$$

$$T = \eta_e * KT * I$$

$$\rightarrow W = \eta_e * KT * I * i * 2 * \pi * \frac{r * \eta_T}{p * g * 2 * R * \cos\theta * (1 - \cos\theta)},$$

Where: theta 'θ' is the internal angle between the member 118 and the surface 412; g is the gravitational force coefficient (a constant); H is the couch frame 110 height; h1 is the base member 116 (sub-pallet) height; h2 is the couch base 436 (not shown previously but the top of the couch base 436 represents the surface 112) height; F is the force applied by the couch frame actuator 122 on the member 118; p is the screw lead associated with a screw (connecting the member 118 to the couch frame actuator 122) driven by the couch frame actuator 122; T is the motor torque associated with the couch frame actuator 122; i is the transmission ratio; $\eta_T$ is the transmission efficiency; $\eta_e$ is the motor efficiency; KT is the motor torque coefficient; I is the electrical current supplied to the couch frame actuator 122; R is the half-length of the member 118; r is the radius of the pivot 120.

In the above expressions, the height of H and motor current of I are variables, and the other parameters are constant. In order to simplify the weight estimation, the height H of couch is assumed to be fixed during estimation of the weight. It is also assumed that the relationship between weight, W, and electrical current, I, is linear. A linear curve may therefore be fitted to actual measurement data of the electrical current. In other words, the electrical current, I, may linearly depend on the weight, W.

Accordingly, the weight may be estimated such that an indication of this weight may be used to determine the shift in accordance with certain methods described herein. Rather than having a separate sensor for measuring the weight, certain embodiments may facilitate a simple way to estimate the weight.

Figure 5:
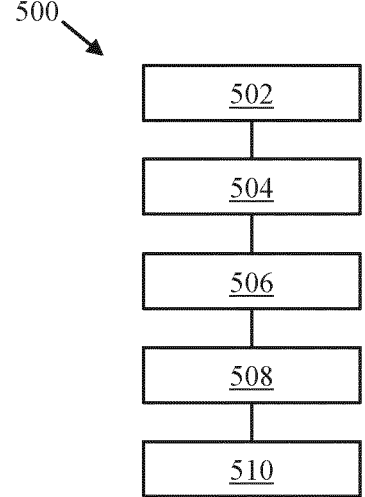
FIG. 5 refers to a method of determining and correcting for couch frame shift according to an embodiment.

FIG. 5 shows a method 500 (e.g., a computer-implemented method) of determining and correcting for couch frame shift according to an embodiment. In this embodiment, the method 500 uses the weight estimation determined according to the model described in relation to FIG. 4, although in other embodiments the weight estimation may be provided by a separate weight sensor (not shown). The method 500 may be implemented in the same way as methods 200, 300 (e.g., using the controller 130). For example, the method 500 may comprise the same or similar functionality as the methods 200 and/or 300. Reference is made to the previous Figures, where appropriate. Certain blocks of the method 500 may not need to be implemented and/or certain blocks of the method 500 may be performed in a different order to that shown by FIG. 5.

The method 500 comprises, at block 502, receiving the indication of the weight by receiving the indication of the electrical current (e.g., the electrical current referred to in FIG. 4).

The method 500 further comprises, at block 504, estimating the weight by using a vertical force balancing model (e.g., as described in relation to FIG. 4) of the electrical current needed to provide the moveable support 106 at a specified height.

The method 500 further comprises, at block 506, receiving a command (e.g., 'L1_cmd') specifying an expected position to which the moveable support 106 is to move to relative to the couch frame 110.

The method 500 further comprises, at block 508, determining an expected shift (e.g., 'L2') of the couch frame according to the shift model (referred to in FIG. 1 and described in more detail below) based on the estimated weight and the expected position (e.g., defined by 'L1').

The method 500 further comprises, at block 510, generating a revised command specifying a modified position to which the moveable support 106 is to move to relative to the couch frame 110 based on a difference between the expected position and the expected shift for the expected position (e.g., 'L1-L2').

A description of how to determine the 'shift model' for determining the couch frame shift is now given.

The shift model is determined by taking measurements of the actual position of the couch frame 110 relative to the imaging apparatus 102 (e.g., a ground reference frame) for a set of (horizontal) positions (in the range 0 to 1800 mm) of the moveable support 106 for each of a set of different weights (75, 135, 185, 217, 274, 307 kg) on the moveable support 106. The 'actual position' may be measured using an independent measurement of the distance between a fixed point on the moveable support 106 (e.g., the end of the moveable support 106 overhanging the couch frame 110 or another appropriate point) and a fixed point defined in relation to the surface 112 (e.g., on the imaging apparatus 102 itself or another appropriate point). Such an independent measurement may be performed by a laser-based position encoder, e.g., using laser-based interferometry.

Thus, in this example, there are six datasets—one for each weight, where the shift (i.e., the difference between actual position and the expected position of the moveable support 106) is measured for a set of positions in the range 0 to 1800 mm.

Figure 6:
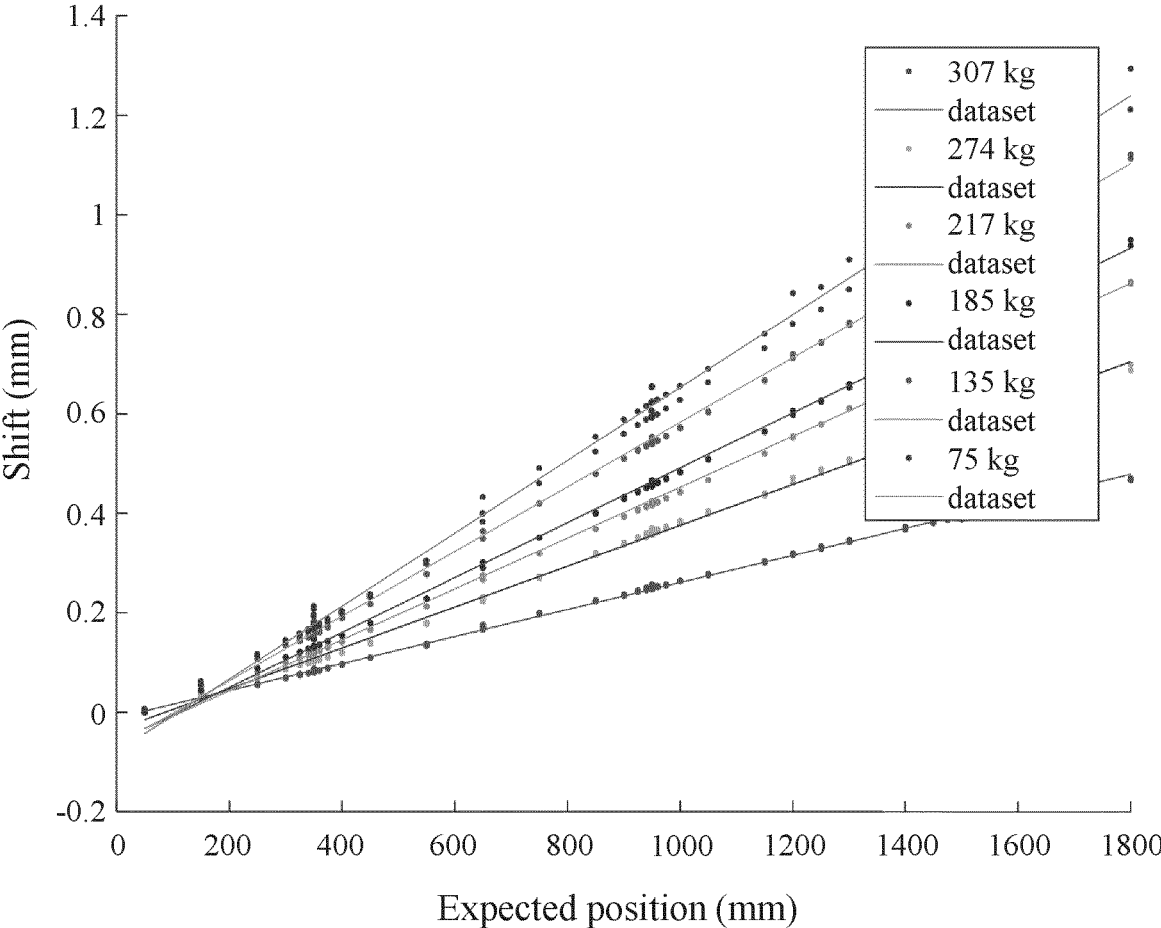
FIG. 6 is a graph depicting a set of measurements of couch shift as a function of the position of a moveable support.

FIG. 6 depicts a graph of the shift (in mm) as a function of the (expected) position (in mm) of the moveable support 106 (relative to the couch frame 110) for each of the six datasets. The steepest curve corresponds to the heaviest weight, 307 kg, while the gentlest curve corresponds to the lightest weight, 75 kg.

As will be recognized, the shift curve is linear and can be fitted with linear function, such as: Y=K(W)*P+D(W), where Y is the measured shift; K(W) is the proportion coefficient (corresponding to the slope of the dataset as a function of the weight, W); P is the expected position of the moveable support 106, D(W) is the offset (corresponding to where the fitted curve intercepts the y-axis). The curve may be fitted with any appropriate algorithm such as a linear regression algorithm. For the depicted datasets, the curve is fitted with confidence bounds of 95%.

In order to obtain a linear function of K(W) and D(W) with respect to the weight, W, K(W) and D(W) are plotted for each weight, as described below.

Figure 7:
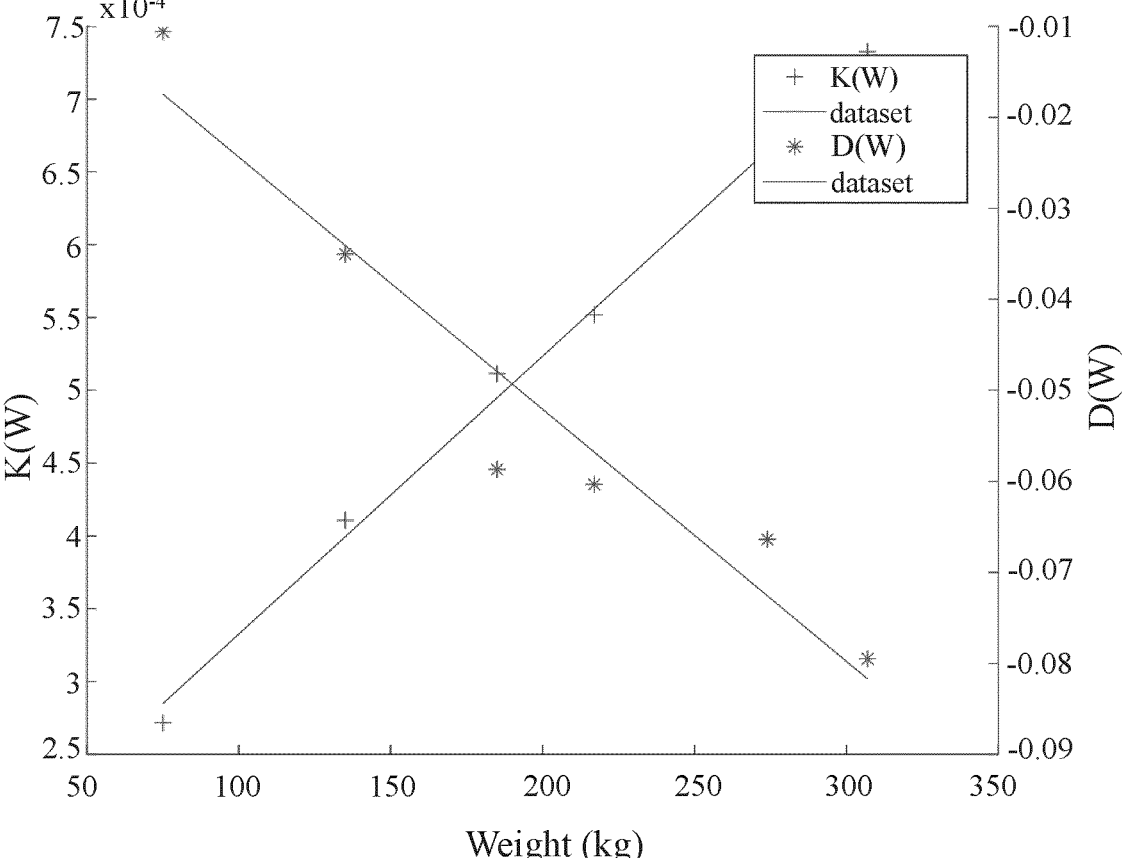
FIG. 7 is graph depicting how to calculate coefficients for a shift model according to an embodiment, based on a curve fitted to the data of FIG. 6.

FIG. 7 depicts a graph plotting K(W) and D(W) as a function of the weight, W, as well as linear curves fitted to each variable. The confidence bounds are 95%. The positive slope shown in FIG. 7 represents K(W), while the negative slope represents D(W). Accordingly, if the weight, W, is estimated as described above, the couch frame shift curve can be determined (as function of the expected position of the moveable support 106) by obtaining K(W) and D(W) for the estimated weight. The values K(W) and D(W) therefore represent a 'shift model' as referred to above.

In other words, the 'shift model' may be represented by a proportion coefficient and an offset fitted to a set of measurement data, where the measurement data comprises an actual measurement of the position of the moveable support 106 (relative to the imaging apparatus 102 or 'ground' reference frame) at each of a set of expected positions of the moveable support 106 (to determine the 'actual' shift). The measurement data can be scaled by weight so that the shift model depends on the weight, e.g., as indicated by the electrical current described above.

Some embodiments relating to the shift model are described below.

In some embodiments, the shift model is determined from a set of measured values for the shift and a corresponding set of indicated values for the position of the moveable support 106 where the shift is measured.

In some embodiments, the shift model is based on a linear function fitted to the set of measured values for the shift and the corresponding set of indicated values for the position of the moveable support 106.

In some embodiments, the shift model is determined from the set of indicated values for the position of the moveable support at each of a set of indicated values for the weight on the moveable support 106.

In order to correct for the shift as determined in accordance with the shift model, the command (e.g., 'L1_cmd') may be modified based on the (expected) position of the moveable support 106. For example, if the command is configured to cause the moveable support 106 to move by a distance 'D1', the shift 'S1' may be estimated using the shift model according to S1=K(W)*D1 (e.g., if the offset is relatively small). Thus, the command may be modified as 'D1−S1', or '(1−K(W))*D1'. In use, the shift model may be used to modify the commands that are otherwise generated and sent to the moveable support actuator 126.

In other words, a command received by the controller 130 to move the moveable support 106 by an (expected) distance, D1, may be modified by the difference between D1 and the (estimated) shift, i.e., D1−S1.

Accordingly, certain embodiments described herein may compensate for motion error introduced by the shift without adding any additional sensors to the set-up. In some embodiments, a force balancing model may be used to estimate the load, or weight, on the moveable support 106. A shift model may be generated based on a set of measurements. The shift model may be used to estimate the couch frame shift for a given position of the moveable support 106 at the estimated weight. Accordingly, certain embodiments may facilitate correction of the motion commands used to drive the moveable support 106 to a specified position such that the subject 104 is more accurately positioned with respect to the imaging apparatus 102 (compared with if the shift is not taken into account).

Figure 8:
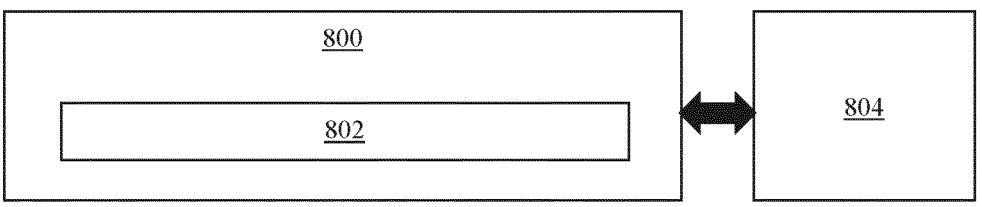
FIG. 8 is a schematic drawing of a machine-readable medium for determining couch frame shift according to an embodiment.

FIG. 8 shows a tangible machine-readable medium 800 according to an embodiment. The tangible machine-readable medium 800 comprises instructions 802 which, when executed on at least one processor 804, cause the at least one processor 804 to implement certain methods described herein (e.g., methods 200, 300, 500). Any of the methods described herein may be implemented by virtue of the tangible machine-readable medium 800 causing the at least one processor 804 to implement such methods.

Figure 9:
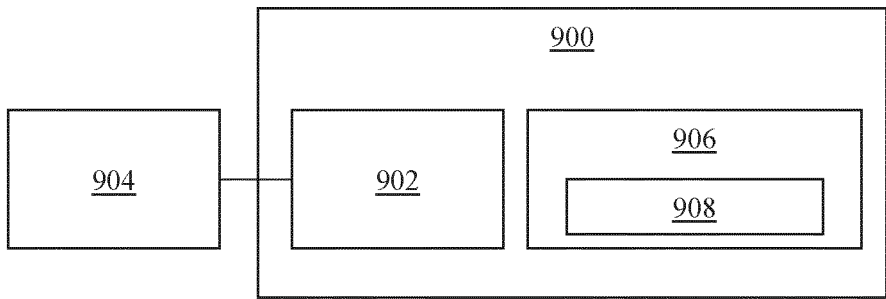
FIG. 9 is a schematic drawing of apparatus for determining and/or correcting couch frame shift according to various embodiments.

FIG. 9 shows apparatus 900 for determining couch frame shift according to various embodiments. The apparatus 900 comprises at least one processor 902 (e.g., implemented by the controller 130 depicted by FIG. 1). The at least one processor 902 is communicatively coupled to an interface 904 for communicating with the couch frame actuator 122 and/or the moveable support actuator 126 (e.g., for receiving information such as electrical current indications and/or sending commands to control the respective actuator 122, 126). In this embodiment, the interface 904 is configured to receive an indication of a weight on the moveable support 106. As indicated previously, the moveable support 106 is moveable relative to the couch frame 110 of the couch assembly 100. The interface 904 may be part of the controller 130 referred to in FIG. 1. Reference is made to certain features of the previous Figures in the description of the apparatus 900.

The apparatus 900 further comprises a tangible machine-readable medium 906 storing instructions 908 readable and executable by the at least one processor 902 to perform a method corresponding to certain methods described herein (e.g., any of the methods 200, 300 and/or 500).

In an embodiment, the instructions 908 are configured to cause the at least one processor 902 to perform the method 200.

In some embodiments relating to the above embodiment, the interface 904 is further configured to receive an indication of an expected position for the moveable support 106 to move to relative to the couch frame 110 to provide the moveable support 106 at a specified position 132 relative to the imaging apparatus 102. The interface 904 may further be configured to send a command to a moveable support actuator 126 of the couch assembly 100. Such a command may be configured to actuate the moveable support actuator 126. In such embodiments, the instructions 908 may be configured to cause the at least one processor 902 to perform the method 300. In the context of the apparatus 900, the method 300 comprises receiving the indication of the expected position; determining the shift for the expected position; and causing the moveable support 106 to move to a modified position determined based on a difference between the expected position and the shift, such that the moveable support 106 is provided at the specified position 132. A 'modified' command generated to cause the moveable support 106 to move is configured to cause the moveable support actuator 126 to move the moveable support 106 to the modified position. The modified command is sent, via the interface 904, to the moveable support actuator 126 to cause actuation of the moveable support actuator 126 according to the command.

In some embodiments, any other method or combination of methods according to the various embodiments described herein may be implemented by storing instructions (e.g., instructions 802, 908) which, when executed by at least one processor 804, 902 cause the method to be implemented.

While the invention has been illustrated and described in detail in the drawings and foregoing description, such illustration and description are to be considered illustrative or exemplary and not restrictive; the invention is not limited to the disclosed embodiments.

One or more features described in one embodiment may be combined with or replace features described in another embodiment.

Embodiments in the present disclosure can be provided as methods, systems or as a combination of machine-readable instructions and processing circuitry. Such machine-readable instructions may be included on a non-transitory machine (for example, computer) readable storage medium (including but not limited to disc storage, CD-ROM, optical storage, etc.) having computer readable program codes therein or thereon.

The present disclosure is described with reference to flow charts and block diagrams of the method, devices, and systems according to embodiments of the present disclosure. Although the flow charts described above show a specific order of execution, the order of execution may differ from that which is depicted. Blocks described in relation to one flow chart may be combined with those of another flow chart. It shall be understood that each block in the flow charts and/or block diagrams, as well as combinations of the blocks in the flow charts and/or block diagrams can be realized by machine readable instructions.

The machine-readable instructions may, for example, be executed by a general-purpose computer, a special purpose computer, an embedded processor, or processors of other programmable data processing devices to realize the functions described in the description and diagrams. In particular, a processor or processing circuitry, or a module thereof, may execute the machine-readable instructions. Thus, functional modules of apparatus and other devices described herein may be implemented by a processor executing machine readable instructions stored in a memory, or a processor operating in accordance with instructions embedded in logic circuitry. The term 'processor' is to be interpreted broadly to include a CPU, processing unit, ASIC, logic unit, or programmable gate array etc. The methods and functional modules may all be performed by a single processor or divided amongst several processors.

Such machine-readable instructions may also be stored in a computer readable storage that can guide the computer or other programmable data processing devices to operate in a specific mode.

Such machine-readable instructions may also be loaded onto a computer or other programmable data processing devices, so that the computer or other programmable data processing devices perform a series of operations to produce computer-implemented processing, thus the instructions executed on the computer or other programmable devices realize functions specified by block(s) in the flow charts and/or in the block diagrams.

Further, the teachings herein may be implemented in the form of a computer program product, the computer program product being stored in a storage medium and comprising a plurality of instructions for making a computer device implement the methods recited in the embodiments of the present disclosure.

Elements or steps described in relation to one embodiment may be combined with or replaced by elements or steps described in relation to another embodiment. Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. A single processor or other unit may fulfil the functions of several items recited in the claims. The mere fact that certain measures are recited in mutually different dependent claims does not indicate that a combination of these measures cannot be used to advantage. A computer program may be stored or distributed on a suitable medium, such as an optical storage medium or a solid-state medium supplied together with or as part of other hardware, but may also be distributed in other forms, such as via the Internet or other wired or wireless telecommunication systems. Any reference signs in the claims should not be construed as limiting the scope.

The invention claimed is:

1. A computer-implemented method, comprising:
   receiving an indication of a weight on a moveable support of a couch assembly, wherein the moveable support is moveable relative to a couch frame of the couch assembly;
   receiving an indication of an expected position for the moveable support to move to a modified position relative to the couch frame to provide the moveable support at a specified position relative to the imaging apparatus; and
   determining, for the expected position, a horizontal shift of the couch frame relative to an imaging apparatus associated with the couch assembly based on a shift model indicative of the horizontal shift as a function of:
   the weight on the moveable support; and
   a horizontal position of the moveable support relative to the couch frame.

2. The method of claim 1, comprising:
   causing the moveable support to move to the modified position based on a difference between the expected position and the horizontal shift, such that the moveable support is provided at the modified position.

3. The method of claim 1, wherein the indication of the weight comprises an indication of electrical current supplied to a couch frame actuator of the couch assembly, wherein the couch frame actuator is configured to control a height of the moveable support relative to a surface supporting the couch assembly.

4. The method of claim 1, further comprising determining the shift model from a set of measured values for the horizontal shift and a corresponding set of indicated values for the horizontal position of the moveable support where the horizontal shift is measured.

5. A non-transitory machine-readable medium comprising instructions which, when executed by at least one processor, cause the at least one processor to perform the method of claim 1.

6. The method of claim 2, wherein causing the moveable support to move to the modified position comprises causing a moveable support actuator of the couch assembly to move the moveable support to the modified position.

7. The method of claim 6, wherein causing the moveable support to move to the modified position comprises:
   generating a command configured to cause the moveable support actuator to move the moveable support to the modified position; and
   sending the command to the moveable support actuator to cause actuation of the moveable support actuator according to the command.

8. The method of claim 6, further comprising using the moveable support actuator to move the moveable support in a horizontal direction relative to a surface supporting the couch assembly, such that the moveable support is provided at the modified position.

9. The method of claim 3, further comprising using the couch frame actuator to maintain the moveable support at a specified height during the horizontal shift of the moveable support relative to the couch frame.

10. The method of claim 3, comprising:

receiving the indication of the weight by receiving the indication of the electrical current;

estimating the weight by using a vertical force balancing model of the electrical current needed to provide the moveable support at a specified height;

receiving a command specifying an expected position to which the moveable support is to move to relative to the couch frame;

determining an expected shift of the couch frame according to the shift model based on the estimated weight and the expected position; and generating a revised command specifying a modified position to which the moveable support is to move to relative to the couch frame based on a difference between the expected position and the expected shift for the expected position.

11. The method of claim 4, wherein the shift model is based on a linear function fitted to the set of measured values for the horizontal shift and the corresponding set of indicated values for the horizontal position of the moveable support.

12. The method of claim 4, wherein the shift model is determined from the set of indicated values for the horizontal position of the moveable support at each of a set of indicated values for the weight on the moveable support.

13. An apparatus, comprising:

an interface configured to receive an indication of a weight on a moveable support of a couch assembly, wherein the moveable support is moveable relative to a couch frame of the couch assembly; and at least one processor communicatively coupled to the interface and configured to execute a plurality of instructions to:

receive the indication of the weight;

receive an indication of an expected position for the moveable support to move to a modified position relative to the couch frame to provide the moveable support at a specified position relative to the imaging apparatus; and determine, for the expected position, a horizontal shift of the couch frame relative to an imaging apparatus associated with the couch assembly based on a shift model indicative of the horizontal shift as a function of:

the weight on the moveable support; and a horizontal position of the moveable support relative to the couch frame.

14. The apparatus of claim 13, wherein:

the interface is further configured to:

send a command to a moveable support actuator of the couch assembly, wherein the command is configured to actuate the moveable support actuator; and wherein the at least one processor is further configured to:

receive the indication of the expected position;

determine the horizontal shift for the expected position; and cause the moveable support to move to a modified position determined based on a difference between the expected position and the horizontal shift, such that the moveable support is provided at the specified position by:

generating the command configured to cause the moveable support actuator to move the moveable support to the modified position; and sending the command, via the interface, to the moveable support actuator to cause actuation of the moveable support actuator according to the command.

* * * * *